United States Patent
Telschow

Patent Number: 5,536,863
Date of Patent: Jul. 16, 1996

[54] (PENTAERYTHRITOL PHOSPHATE ALCOHOL) (CYCLIC NEOPENTYLENE GLYCOL) PHOSPHITE AND PHOSPHONATE

[75] Inventor: Jeffrey E. Telschow, Tarrytown, N.Y.

[73] Assignee: Akzo Nobel N.V., Arnhem, Netherlands

[21] Appl. No.: 438,152

[22] Filed: May 9, 1995

[51] Int. Cl.$^6$ .................................................. C07F 9/09
[52] U.S. Cl. ................................................... 558/74
[58] Field of Search ........................................ 558/74

[56] References Cited

U.S. PATENT DOCUMENTS

| | | | |
|---|---|---|---|
| 3,725,510 | 4/1973 | Dever et al. | 260/927 R |
| 3,922,323 | 11/1975 | Reese et al. | 260/927 R |
| 4,169,118 | 9/1979 | Demarcq | 260/927 R |
| 4,427,813 | 1/1984 | McEwen et al. | 524/119 |
| 4,956,406 | 9/1990 | Myers et al. | 524/119 |
| 5,362,898 | 11/1994 | Telschow | 558/74 |
| 5,420,326 | 5/1995 | Telschow | 558/74 |

OTHER PUBLICATIONS

Derwent Pat. Abstr. 88–206316/30, abstracting DE 3700373 (published Jul. 21, 1988).

*Primary Examiner*—Johann Richter
*Assistant Examiner*—Laura L. Stockton
*Attorney, Agent, or Firm*—Richard P. Fennelly; Louis A. Morris

[57] ABSTRACT

(Pentaerythritol phosphate alcohol)(cyclic neopentylene glycol) phosphite and phosphonate are disclosed as flame retardant compounds. The first named compound is formed by the reaction of pentaerythritol phosphate alcohol with a neopentylene glycol halophosphite, such as neopentylene glycol chlorophosphite. The (pentaerythritol phosphate alcohol)(cyclic neopentylene glycol) phosphonate is formed by heating (pentaerythritol phosphate ol)(cyclic neopentylene glycol) phosphite.

2 Claims, No Drawings

(PENTAERYTHRITOL PHOSPHATE ALCOHOL) (CYCLIC NEOPENTYLENE GLYCOL) PHOSPHITE AND PHOSPHONATE

BACKGROUND OF THE INVENTION

Various derivatives of pentaerythritol phosphate are known as flame retardant additives for polymers such as polypropylene. A recent example is provided by U.S. Pat. No. 4,801,625 to W. J. Parr et al. which describes ether, ester and carbonate derivatives of pentaerythritol phosphate. The carbonate version of such compounds can be advantageously prepared by the reaction of pentaerythritol phosphate alcohol with a dihydrocarbyl carbonate as described in U.S. Pat. No. 5,235,085.

SUMMARY OF THE INVENTION

The invention relates to (pentaerythritol phosphate alcohol)(cyclic neopentylene glycol)phosphite and (pentaerythritol phosphate alcohol)(cyclic neopentylene glycol)phosphonate which are useful as flame retardant compounds. The first named compound is formed by the reaction of pentaerythritol phosphate alcohol ("PEPA") with a neopentylene glycol halophosphite, such as neopentylene glycol chlorophosphite. The (pentaerythritol phosphate alcohol-)(cyclic neopentylene glycol) phosphonate is formed by heating (pentaerythritol phosphate alcohol)(cyclic neopentylene glycol) phosphite.

U.S. Pat. No. 5,362,898 discloses certain bis(pentaerythritol phosphate alcohol) alkylphosphonate compounds, such as those containing from about one to about four carbon atoms in their alkyl moiety, with bis(pentaerythritol phosphate alcohol) methylphosphonate being a preferred species thereof.

DESCRIPTION OF THE PREFERRED EMBODIMENTS

The present novel (pentaerythritol phosphate alcohol) (cyclic neopentylene glycol) phosphite compound is of the formula:

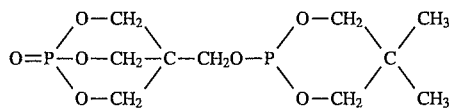

and the novel (pentaerythritol phosphate alcohol) (cyclic neopentylene glycol) phosphonate compound is of the formula:

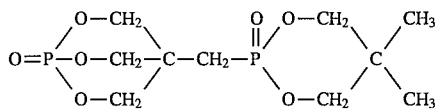

One process for forming the above-described novel phosphite compound is by the reaction of a neopentylene glycol halophosphite with pentaerythritol phosphate alcohol which has the formula

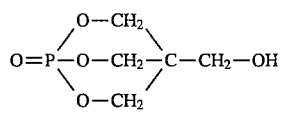

The neopentylene glycol halophosphite reagent is of the formula

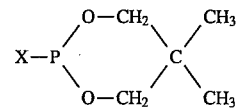

where X is a halogen atom, such as chlorine. The reaction can be conducted at room temperature in an appropriate organic solvent, such as acetonitrile using an acid acceptor, such as a trialkylamine.

Once the phosphite compound has been synthesized, it can be converted to the novel phosphonate compound of the present invention by heating, for example, in a high boiling organic solvent, such as an aryl phosphate solvent.

The present invention is further understood by reference to the Examples which follow.

EXAMPLE 1

In a 250 mL, mechanically stirred, four-necked flask fitted with pot thermometer, condenser and dropping funnel were placed 18.0 grams (0.10 mole) of pentaerythritol phosphate alcohol (PEPA), 13.9 mL (10.1 grams, 0.10 mole) of triethylamine, and 75 mL of dry acetonitrile. Then, 16.9 grams (0.10 mole) of neopentylene chlorophosphite (2-chloro-5,5-dimethyl-1,3,2-dioxaphosphorinane) was added dropwise from the funnel over twenty minutes, while maintaining the temperature of the stirred reaction mixture at 20°–30° C. under nitrogen. The mixture was allowed to stir for twenty-two hours at ambient temperature, the white solid which had formed was filtered and was dissolved in 300 mL of methylene chloride and was then extracted three times with 100 mL of water. On evaporation of the methylene chloride, 14.1 grams of a white powder with a melting point of 200°–203° C. remained. The solid exhibited two equally intense singlets by $^{31}$P NMR ($d_6$-DMSO) at +122.7 and −6.2 ppm, consistent with the desired PEPA-NPG phosphite product (5,5-dimethyl-2-(2-oxo-2,6,7-trioxa-1-phosphabicyclo [2.2.2]oct-4ylmethoxy)-1,3,2-dioxaphosphorinane).

EXAMPLE 2

In a 100 mL, mechanically stirred, four-necked flask fitted with pot thermometer, were placed 11.4 grams (0.0367 mole) of the PEPA-NPG phosphite from Example 1, 20 mg of iodine, and 30 mL of Phosflex® 41P under nitrogen. The solution was heated for sixteen hours at 210° C. to promote Arbuzov rearrangement. Analysis using $^{31}$P NMR ($d_6$-DMSO) revealed two resonances at +19.3 and −7.1 ppm, corresponding to the desired PEPA-NPG phosphonate product (5,5-dimethyl-2-(2-oxo-2,6,7-trioxa-1-phosphabicyclo [2.2.2]oct-4ylmethyl)-1,3,2-dioxaphosphorinane, 2-oxide).

The foregoing Examples are intended to illustrate certain embodiments of the present invention and, for that reason, should not be construed in a limiting sense. The scope of protection sought is set forth in the claims which follow.

I claim:

1. (Pentaerythritol phosphate alcohol)(cyclic neopentylene glycol) phosphite.
2. (Pentaerythritol phosphate alcohol)(cyclic neopentylene glycol) phosphonate.

* * * * *